United States Patent
Mansour et al.

(10) Patent No.: US 10,603,402 B2
(45) Date of Patent: Mar. 31, 2020

(54) ELASTIC ADHESIVE COMPOSITION AND AN ELASTIC COMPOSITE MADE WITH THE SAME

(71) Applicant: H.B. Fuller Company, St. Paul, MN (US)

(72) Inventors: Ameara S. Mansour, Woodbury, MN (US); Kevin P. Davis, Woodbury, MN (US); David B. Malcolm, Maplewood, MN (US)

(73) Assignee: H.B. Fuller Company, St. Paul, MN (US)

( * ) Notice: Subject to any disclaimer, the term of this patent is extended or adjusted under 35 U.S.C. 154(b) by 250 days.

(21) Appl. No.: 15/072,041

(22) Filed: Mar. 16, 2016

(65) Prior Publication Data

US 2016/0271291 A1 Sep. 22, 2016

Related U.S. Application Data

(60) Provisional application No. 62/133,798, filed on Mar. 16, 2015.

(51) Int. Cl.
| | | |
|---|---|---|
| *A61L 15/58* | (2006.01) | |
| *C09J 153/02* | (2006.01) | |
| *B32B 7/12* | (2006.01) | |
| *B32B 27/08* | (2006.01) | |
| *B32B 5/02* | (2006.01) | |
| *B32B 5/08* | (2006.01) | |
| *B32B 27/12* | (2006.01) | |
| *A61F 13/49* | (2006.01) | |
| *B32B 5/26* | (2006.01) | |
| *B32B 5/04* | (2006.01) | |
| *C09J 7/38* | (2018.01) | |
| *A61L 15/24* | (2006.01) | |
| *B32B 5/24* | (2006.01) | |
| *B32B 25/10* | (2006.01) | |
| *B32B 25/16* | (2006.01) | |

(52) U.S. Cl.
CPC ........ *A61L 15/58* (2013.01); *A61F 13/49009* (2013.01); *A61L 15/24* (2013.01); *B32B 5/022* (2013.01); *B32B 5/04* (2013.01); *B32B 5/08* (2013.01); *B32B 5/24* (2013.01); *B32B 5/26* (2013.01); *B32B 7/12* (2013.01); *B32B 25/10* (2013.01); *B32B 25/16* (2013.01); *B32B 27/08* (2013.01); *B32B 27/12* (2013.01); *C09J 7/387* (2018.01); *C09J 153/02* (2013.01); *B32B 2255/02* (2013.01); *B32B 2255/26* (2013.01); *B32B 2262/0253* (2013.01); *B32B 2262/0261* (2013.01); *B32B 2262/0284* (2013.01); *B32B 2262/04* (2013.01); *B32B 2262/062* (2013.01); *B32B 2262/065* (2013.01); *B32B 2262/14* (2013.01); *B32B 2264/00* (2013.01); *B32B 2307/51* (2013.01); *B32B 2437/00* (2013.01); *B32B 2535/00* (2013.01); *B32B 2555/02* (2013.01); *C09J 2201/122* (2013.01); *C09J 2201/606* (2013.01); *C09J 2201/61* (2013.01); *C09J 2425/00* (2013.01); *C09J 2453/00* (2013.01)

(58) Field of Classification Search
CPC .... A61F 13/00; A61F 13/49009; A61L 15/58; A61L 15/24; C09J 7/0221; C09J 2425/00; C09J 2453/00; C09J 7/35–7/38; C09J 7/387; C09J 125/04–125/14; C09J 153/00–153/025; C09J 2201/61; B32B 5/022; B32B 5/04; B32B 5/24; B32B 5/26; B32B 7/12; B32B 2255/02; B32B 2255/26; B32B 2307/51; B32B 2535/00; B32B 2555/02; B32B 27/302; B32B 2037/1215; B65H 2301/51132; C08L 25/08–25/14; D06M 15/233
USPC .................. 442/328, 381, 384, 387, 408
See application file for complete search history.

(56) References Cited

U.S. PATENT DOCUMENTS

| | | |
|---|---|---|
| 4,543,099 A | 9/1985 | Bunnelle et al. |
| 4,789,699 A | 12/1988 | Kieffer et al. |
| 5,149,741 A | 9/1992 | Alper et al. |
| 5,342,858 A * | 8/1994 | Litchholt .......... C08J 9/30 521/98 |
| 5,536,563 A | 7/1996 | Shah et al. |
| 6,025,071 A | 2/2000 | Cameron |
| 6,103,814 A | 8/2000 | vanDrongelen |

(Continued)

FOREIGN PATENT DOCUMENTS

| | | |
|---|---|---|
| EP | 0802949 | 5/2003 |
| EP | 1411100 | 4/2004 |
| WO | WO96/011236 | 4/1996 |

OTHER PUBLICATIONS

"Section III: Physical Properties of Monomers and Solvents." Polymer Handbook, by E. H. Immergut et al., 4th ed., Wiley, 2005, pp. 34-36. (Year: 2005).*
"Temperature and Pressure Dependence of Viscosity." Polymer Testing, by Wolfgang Grellmann and Sabine Seidler, Hanser Publishers, 2007, pp. 46-46. https://app.knovel.com/hotlink/pdf/id:kt008VJCN5/polymer-testing/molecular-mass-influence (Year: 2007).*

(Continued)

*Primary Examiner* — Laura C Powers
*Assistant Examiner* — Larissa Rowe Emrich
(74) *Attorney, Agent, or Firm* — Kirsten Stone; Kristi Halloran

(57) ABSTRACT

This invention claims hot melt adhesive compositions that can be used to form elastic composites that are useful in disposable absorbent articles. The compositions have good elastic recovery and high peel adhesion at a viscosity of less than about 20,000 cps at 177° C. The low viscosity makes it possible to apply the adhesive at a high line speed and target application to only those areas requiring elastic performance.

20 Claims, No Drawings

(56) References Cited

U.S. PATENT DOCUMENTS

| | | | |
|---|---|---|---|
| 6,120,887 A | 9/2000 | Werenicz | |
| 6,162,859 A * | 12/2000 | Lu | C08L 53/02 |
| | | | 524/505 |
| 6,184,285 B1 | 2/2001 | Hatfield et al. | |
| 6,245,050 B1 | 6/2001 | Odorzynski et al. | |
| 6,430,898 B1 * | 8/2002 | Remmers | B29B 13/022 |
| | | | 53/140 |
| 6,497,696 B1 | 12/2002 | Freiburger et al. | |
| 6,503,239 B1 | 1/2003 | Bruemmer-Prestley et al. | |
| 6,531,544 B1 | 3/2003 | Vaughan | |
| 6,533,765 B1 | 3/2003 | Blaney et al. | |
| 6,582,829 B1 | 6/2003 | Quinn et al. | |
| 6,702,798 B2 | 3/2004 | Christoffel et al. | |
| 6,967,178 B2 | 11/2005 | Zhou | |
| 7,000,260 B2 | 2/2006 | Rajala et al. | |
| 7,015,155 B2 | 3/2006 | Zhou et al. | |
| 7,207,979 B2 | 4/2007 | Price et al. | |
| 7,297,139 B2 | 11/2007 | Price et al. | |
| 7,316,842 B2 | 1/2008 | Zhou et al. | |
| 7,329,621 B2 | 2/2008 | Collier et al. | |
| 7,439,301 B2 | 10/2008 | Handlin, Jr. | |
| 7,621,900 B2 | 11/2009 | Van Gompel et al. | |
| 7,651,765 B2 | 1/2010 | De Keyzer | |
| 7,717,893 B2 | 5/2010 | Hird et al. | |
| 7,749,211 B2 | 7/2010 | Van Gompel et al. | |
| 7,795,336 B2 | 9/2010 | Paul et al. | |
| 7,799,863 B2 | 9/2010 | He et al. | |
| 7,887,526 B2 | 2/2011 | Van Gompel et al. | |
| 7,923,505 B2 | 4/2011 | Zhou et al. | |
| 8,147,476 B2 | 4/2012 | Veith et al. | |
| 8,163,824 B2 | 4/2012 | Okazaki et al. | |
| 8,257,334 B2 | 9/2012 | Buell | |
| 8,277,430 B2 | 10/2012 | Tabor et al. | |
| 8,324,309 B2 | 12/2012 | Dubois | |
| 8,377,023 B2 | 2/2013 | Sawyer | |
| 8,450,555 B2 | 5/2013 | Nhan et al. | |
| 8,664,469 B2 | 3/2014 | Veith et al. | |
| 8,920,400 B2 | 12/2014 | Veith | |
| 9,011,401 B2 | 4/2015 | Kamiyama | |
| 9,056,975 B2 | 6/2015 | Chapman et al. | |
| 9,296,930 B2 | 3/2016 | Hu et al. | |
| 2002/0015812 A1 * | 2/2002 | Littleton | A41D 19/0058 |
| | | | 428/36.8 |
| 2003/0168165 A1 * | 9/2003 | Hatfield | A61L 15/585 |
| | | | 156/327 |
| 2004/0005834 A1 * | 1/2004 | Zhou | A61F 13/15593 |
| | | | 442/328 |
| 2004/0162394 A1 | 8/2004 | Bunnelle et al. | |
| 2005/0054779 A1 | 3/2005 | Zhou | |
| 2006/0246804 A1 * | 11/2006 | Thomas | A61F 13/4902 |
| | | | 442/328 |
| 2007/0117934 A1 | 5/2007 | He et al. | |
| 2008/0038982 A1 * | 2/2008 | Motomura | B32B 5/26 |
| | | | 442/382 |
| 2008/0076860 A1 | 3/2008 | Ahmed | |
| 2008/0081858 A1 * | 4/2008 | Okazaki | C09J 153/02 |
| | | | 524/274 |
| 2009/0088718 A1 | 4/2009 | Toyoshima | |
| 2010/0049313 A1 | 9/2010 | Okazaki et al. | |
| 2012/0149827 A1 | 6/2012 | Yuhong et al. | |
| 2012/0226250 A1 * | 9/2012 | Sato | A61F 13/51104 |
| | | | 604/367 |
| 2013/0202787 A1 | 8/2013 | Hu et al. | |
| 2013/0225020 A1 | 8/2013 | Flood et al. | |
| 2013/0299731 A1 * | 11/2013 | Wright | C08K 3/22 |
| | | | 252/62 |
| 2014/0357145 A1 | 12/2014 | Remmers | |
| 2014/0364532 A1 | 12/2014 | Dubois et al. | |
| 2015/0017868 A1 | 1/2015 | Stafeil et al. | |
| 2016/0067116 A1 | 3/2016 | Beckman | |
| 2016/0067117 A1 | 3/2016 | Beckman | |
| 2016/0068721 A1 | 3/2016 | Malcolm | |
| 2016/0376482 A1 | 12/2016 | Morgeneyer | |
| 2017/0157888 A1 | 6/2017 | Ikishima et al. | |

OTHER PUBLICATIONS

Chodák I. (1999) Hard-elastic or 'springy' polypropylene. In: Karger-Kocsis J. (eds) Polypropylene. Polymer Science and Technology Series, vol. 2. Springer, Dordrecht. https://rd.springer.com/content/pdf/10.1007%2F978-94-011-4421-6_41.pdf (Year: 1999).*

Benedek, Pressure-Sensitive Adhesives and Applications, 2nd ed., Ch.6, 2004.

Kraton Innovations, "MD1648:A New Addition to the Kraton™ ERS Polymer Family", Market Launch Package. May 2014, pp. 1-20.

HASO USA Inc. Product Brochure, "Haso Underwear" Body Form 360α™.

Shawn W. Mowry, PhD., "New High-Efficiency Styrenic Block Copolymers, Tackifier for Adhesives"; Adhesives Magazine; Jan. 2009.

* cited by examiner

ELASTIC ADHESIVE COMPOSITION AND AN ELASTIC COMPOSITE MADE WITH THE SAME

This application claims the benefit of U.S. Provisional Application No. 62/133,798, filed Mar. 16, 2015, which is incorporated herein.

BACKGROUND

Adhesives are often used to bond substrates together. In the area of industrial adhesives, hot melt adhesives are commonly used to bond together a wide variety of articles including disposable absorbent articles comprising nonwoven substrates e.g. diapers, training paints, surgical garments, swim wear, absorbent underpants, adult incontinence products, sanitary napkins and medical dressings (e.g. wound care products).

There can be multiple hot melt adhesives used in the manufacture of a disposable absorbent article. For example, in the manufacture of a disposable diaper, hot melt adhesives are used for construction (e.g. bonding the backsheet to the nonwoven and optionally the absorbent pad), elastic attachment (e.g. bonding the elastic material to the backsheet in for example the leg or waist area), and for the core stabilization (e.g. applying an adhesive to the absorbent core to increase the strength of the core).

Hot melt adhesives can also be used to form elastic composites that are useful in disposable articles. Currently, elastic composites are often formed in a 5-layer configuration including the following layers: nonwoven, hot melt adhesive, elastic material, hot melt adhesive, nonwoven. The hot melt adhesive bonds the non adhesive elastic to the nonwoven to form a composite.

Alternately, a hot melt adhesive with elastic properties can replace both the elastic material and the adhesive layers to form a simplified 3-layer elastic composite that can impart stretch to various portions of the disposable article.

Styrene block copolymers have been used as a polymer in such compositions.

Melt flow rate (MFR) is inversely related to the viscosity of a polymer. A high MFR means that a polymer has a low viscosity. Commercially available styrene block copolymers (SBC) work well in adhesives, but are not commonly commercially available with a high melt flow rate (i.e. >than 15 g/10 min (190° C., 2.16 kgs)). The few grades that are available, generally achieve the high melt flow rate with a high di-block content, which lowers the mechanical properties of the polymer, and those of the adhesive as well. This makes it difficult to formulate a low viscosity hot melt adhesive with good elastic recovery and high peel adhesion.

It would be desirable to be able to formulate a low viscosity hot melt adhesive based on SBC, with good elastic recovery so as to be useful in constructing a 3-layer elastic composite.

SUMMARY

In one aspect, the invention includes an elastic composite including: a first and second substrate; and a hot melt adhesive composition between the first and second substrates thereby permanently bonding the first and second substrates to each other and providing elasticity in the bonded area, said hot melt adhesive composition including: at least 15% by weight of a first styrene block copolymer with a melt flow rate of at least about 15 g/10 minutes (190° C., 2.16 kgs) and a diblock content of no greater than about 10% by weight, wherein the hot melt adhesive composition has a viscosity of no greater than about 7,000 cps at 177° C.

In one embodiment, the elastic composite includes a hot melt adhesive composition that has a set after 50% hysteresis of no more than about 10%. In a different embodiment, the elastic composite includes a hot melt adhesive composition that has a viscosity of no greater than about 5,000 cps at 177° C. in another embodiment, the first styrene block copolymer has an average styrene content of at least about 18% by weight. In one embodiment, the elastic composite includes a hot melt adhesive composition further comprises a tackifying agent. In a different embodiment, the hot melt adhesive includes a first styrene block copolymer that has an unsaturated mid-block.

In one embodiment, the elastic composite includes first and second substrate that are nonwoven. In another embodiment, the nonwoven is airlaid, carded and hydroentangled. In a different embodiment, the nonwoven is extensible to greater than 100% in the cross web direction.

In one embodiment, the hot melt adhesive is applied to the substrate using an application method selected from the group consisting of slot and non contact coating. In a different embodiment, the hot melt adhesive is applied to the substrate using an application method selected from the group consisting of screen printing, spraying, comb shim slot and gravure roll.

In one embodiment, a disposable article includes the claimed elastic composite. In another embodiment, the elastic composite is used in an application selected from the group consisting of ear, waist band, belly band and side panel. In a different embodiment, the disposable article is selected from the group consisting of diaper, adult incontinence product, feminine hygiene product and medical bandage.

In one aspect, the invention features a hot melt adhesive composition that can be used to create a bonded, elasticized region, including from about 50% to about 70% by weight styrene block copolymer, the styrene block copolymer including at least about 20% by weight, based on the weight of the composition, of a first styrene block copolymer having a melt flow rate of at least about 15 g/10 minutes (190° C., 2.16 kgs) and a diblock content of no greater than about 10% by weight, a tackifying agent and, no greater than about 15% by weight plasticizer, the adhesive composition having a viscosity of no greater than about 20,000 cps at 177° C.

In another embodiment, the hot melt adhesive composition has a Viscosity Ratio (Viscosity @ 149° C. (cps)/Viscosity @ 177° C. (cps)) of no greater than about 5. In a different embodiment, the hot melt adhesive composition has a viscosity of no greater than about 15,000 cps at 177° C. In one embodiment, the styrene content of the first styrene block copolymer is at least about 18% by weight. In another embodiment, the first styrene block copolymer has a MFR (190° C./2.16 kg) of at least about 50.

In a different embodiment, the invention features, an elastic composite including: a substrate, and the hot melt adhesive composition bonded to the substrate; wherein the hot melt adhesive provides elasticity to the bonded area.

Other features and advantages will be apparent from the following description of the preferred embodiments and from the claims.

DETAILED DESCRIPTION

Applicants have discovered hot melt adhesive compositions that can be used to form elastic composites that are useful in disposable articles (e.g. disposable absorbent articles). The compositions have good elastic recovery and high peel adhesion and have a viscosity of no greater than about 20,000 cps at 177° C. The low viscosity makes it possible to apply the adhesive at a high line speed and target application to only those areas requiring elastic performance.

Elastic Composite

The elastic composite can include a first substrate and a hot melt adhesive composition. The hot melt adhesive composition imparts elasticity to the first substrate.

Alternately, the elastic composite can include a first substrate, a second substrate and a hot melt adhesive composition. The hot melt adhesive composition is present between the first and second substrate, permanently bonding the substrates to each other and providing elasticity in the bonded area.

At least one of the substrates is selected from the group consisting of nonwoven and polymer film.

Any nonwoven can be used. The nonwoven can be an elastic nonwoven (e.g. core and shell type). The nonwoven can contain fibers made from one or more polymers e.g. PET (polyethylene terephthalate), PBT (polybutylene terephthalate), nylon, polypropylene and polyethylene), one or more natural fibers (e.g. rayon cellulose, cotton cellulose, hemp and viscose) or combinations thereof. The nonwoven can be formed by a number of different methods, including e.g. airlaid, wetlaid, spunbound or meltblown. The fibers can be carded (e.g. run through a comb) so that they are oriented in a particular direction. The webs can be bonded together in any manner including e.g. hydroentangled, chemical bonded, needle punched or thermally bonded. In one embodiment, the nonwoven is comprised of a blend of polypropylene and PET fibers which are airlaid, carded and hydroentangled.

Any polymer film can be used. The polymer film can be selected from the group consisting of polyethylene, polypropylene, polyethylene copolymers, polypropylene copolymers, and PET.

The first and second substrates can be nonwoven. The nonwoven can have a basis weight of less than 40 grams per square meter (gsm), less than 35 gsm, or even less than about 30 gsm. The nonwoven can be extensible to greater than 100% in the cross-web direction.

Various post treatments, such as treatment with grooved rolls activation can be used to adjust the mechanical properties (e.g. extensibility) of the composite.

The adhesive can be applied to the first and or second substrate using a variety of application methods including slot coating, non-contact coating, spraying including, e.g., spiral spraying and random spraying, screen printing, foaming, engraved roller, gravure roller, extrusion and meltblown.

The adhesive can be applied to one substrate.

Alternatively, the adhesive can be applied to the first substrate and then contacted by the second substrate to form the composite. Pressure or tension can be used to aid in forming the bonded composite. The composite can be formed within a disposable article manufacturing process. Alternatively, the composite is formed prior to the disposable article manufacturing process.

Adhesive Composition

The adhesive composition is a hot melt adhesive. The adhesive can be a pressure sensitive adhesive. The adhesive composition can be light in color and can have good thermal stability. The adhesive can have an initial Gardner Color after manufacturing of less than about 3, or even less than about 2. Alternately, the adhesive can be pigmented to an opaque color such as e.g. pink, blue, white, etc.

The adhesive composition has low viscosity at application temperature. The viscosity is no greater than about 20,000 cps at around 177° C., no greater than about 15,000 cps at around 177° C., no greater than about 10,000 cps at around 177° C., no greater than about 7,000 cps at around 177° C., no greater than about 5,000 cps at around 177° C., from about 500 cps to about 20,000 cps at around 177° C., or even from about 1,000 cps to about 15,000 cps at around 177° C. The adhesive composition gives a set after 50% hysterisis of no more than about 20%, no more than about 12%, or even no more than about 10%.

The adhesive composition can have a Force Relaxation of no greater than 4.75 newtons, no greater than 4.50 newtons, or even no greater than 4.25 newtons.

The adhesive composition provides good adhesion when tested according to the Peel Force Test Method. In some embodiments, the adhesive has peel adhesion of greater than about 100 grams/inch, greater than about 200 grams/inch, or even greater than about 300 grams/inch. In other embodiments the substrates tear when peeled SF (substrate failure).

The adhesive composition can have a viscosity curve with a Viscosity Ratio (Viscosity @ 149° C. (cps)/Viscosity @ 177° C.) that is no greater than about 7.5, no greater than about 6, no greater than about 5, or even no greater than about 4. A low viscosity ratio can indicate improved machining at high line speeds as the adhesive does not gain viscosity quickly as it cools.

The adhesive composition can include a tackifying resin with at least some aromatic content and a naphthenic oil.

Styrene Block Copolymer

First Styrene Block Copolymer

The hot melt adhesive composition includes a first styrene block copolymer with a melt flow rate of at least about 15 g/10 minutes (190° C., 2.16 kgs), at least about 20 g/10 minutes (190° C., 2.16 kgs), at least about 30 g/10 minutes (190° C., 2.16 kgs), at least about 50 g/10 minutes (190° C., 2.16 kgs) or even from about 15 to about 200. The first styrene block copolymer has a diblock content of no greater than about 10% by weight, no greater than about 5% by weight, no greater than about 3% by weight, or even no greater than about 1% by weight.

The composition can include one or more than one first styrene block copolymers with a melt flow rate of at least about 15 g/10 minutes (190° C., 2.16 kgs) and a diblock content of no greater than about 10% by weight.

The first styrene block copolymer is present at, at least about 10% by weight, at least about 15% by weight, at least about 20% by weight, from about 10% to about 70% by weight, or even from about 15% to about 65% by weight.

The first styrene block copolymer includes an aromatic vinyl polymer block and a conjugated diene polymer block, a hydrogenated conjugated diene polymer block, or a combination thereof. The blocks can be arranged in a variety of configurations including, e.g., linear, branched, radial, star and combinations thereof. The aromatic vinyl polymer block can be derived from a variety of aromatic vinyl compounds including, e.g., styrene, alpha-methylstyrene, beta-methylstyrene, o-, m-, p-methylstyrene, t-butylstyrene-2,4,6-trimethylstyrene, monofluorostyrene, difluorostyrene, monochlorostyrene, dichlorostyrene, methoxystyrene, 1,3-vinylnaphthalene, vinylanthracene, indene, acenaphthylene, and combinations thereof. The diene polymer block can be derived from a variety of diene-containing compounds including, e.g., isoprene, butadiene, hexadiene, 2,3-dimethyl-1,3-butadiene, 1,3-pentadiene, and hydrogenated versions thereof, and combinations thereof.

Useful first styrene block copolymers include, e.g., triblock, multi-arm, and radial copolymers including, e.g., styrene-butadiene-styrene (SBS), styrene-isoprene-styrene (SIS), styrene-butadiene-isobutylene-styrene (SBBS), styrene-isoprene-butadiene-styrene (SIBS), styrene-ethylene/butene-styrene (SEBS), styrene-ethylene/propylene-styrene (SEPS), styrene-ethylene-ethylene/propylene-styrene (SEEPS), and combinations thereof.

The first styrene block copolymer can have a styrene content of at least about 18% by weight, at least about 25% by weight, at least about 30% by weight, no greater than about 35% by weight, no greater than about 40% by weight, from about 30% to about 40% by weight, from about 30% to about 37% by weight, from about 18% by weight to about 35% by weight, from about 25% by weight to about 35% by weight, or even from about 30% to about 35% by weight.

The first styrene block copolymer can have an unsaturated mid-block, alternately the mid-block can be saturated i.e. hydrogenated. The first styrene block copolymer can be selected from the group consisting of SIS, SBS, SIBS, and SBBS.

The first styrene block copolymer can be the only polymer present in the adhesive.

Useful first styrene block copolymers include for example KRATON MD 1648 commercially available from Kraton Polymers US LLC (Houston, Tex.).

The composition can include additional styrene block copolymers. Useful additional styrene block copolymers include VECTOR 4411 and VECTOR 6241 available from TSRC Corporation (Houston, Tex.), SOLPRENE 411 (a high molecular weight radial SBS block copolymer) available from Dynasol (Houston, Tex.). The adhesive composition includes a total styrene block copolymer content (including the first styrene block copolymer and any others) of at least about 35% by weight, at least about 40% by weight, from about 35% by weight to about 60% by weight, or even from about 50% by weight to about 70% by weight.

Tackifying Agent

The adhesive includes a tackifying agent. The tackifying agent can be fluid or solid at room temperature. Suitable classes of tackifying agents include, e.g., aromatic, aliphatic and cycloaliphatic hydrocarbon resins, mixed aromatic and aliphatic modified hydrocarbon resins, aromatic modified aliphatic hydrocarbon resins, and hydrogenated versions thereof; terpenes, modified terpenes and hydrogenated versions thereof; natural rosins, modified rosins, rosin esters, and hydrogenated versions thereof; low molecular weight polylactic acid; and combinations thereof. Examples of useful natural and modified rosins include gum rosin, wood rosin, tall oil rosin, distilled rosin, hydrogenated rosin, dimerized rosin and polymerized rosin. Examples of useful rosin esters include e.g., glycerol esters of pale wood rosin, glycerol esters of hydrogenated rosin, glycerol esters of polymerized rosin, pentaerythritol esters of natural and modified rosins including pentaerythritol esters of pale wood rosin, pentaerythritol esters of hydrogenated rosin, pentaerythritol esters of tall oil rosin, and phenolic-modified pentaerythritol esters of rosin.

Useful tackifying agents are commercially available under a variety of trade designations including, e.g., the ESCOREZ series of trade designations from Exxon Mobil Chemical Company (Houston, Tex.) including ESCOREZ 5400 (1% aromatic content), ESCOREZ 5415, ESCOREZ 5600 (9.8% aromatic content), ESCOREZ 5690 (10% aromatic content), ESCOREZ 5615 (9.9% aromatic content), the EASTOTAC series of trade designations from Eastman Chemical (Kingsport, Tenn.) including EASTOTAC H-100R and EASTOTAC H-100L, and the WINGTACK series of trade designations from Cray Valley HSC (Exton, Pa.) including WINGTACK 86, WINGTACK EXTRA, and WINGTACK 95 and the PICCOTAC and KRISTALEX series of trade designations from Eastman Chemical Company (Kingsport, Tenn.) including, e.g., PICCOTAC 8095 and KRISTALEX 3100.

The adhesive can be free from end block resin that has a melting point greater than about 110° C., greater than about 120° C., or even greater than about 130° C.

The adhesive composition can include at least one tackifying agent with aromatic content. The tackifying agent can have an aromatic content of greater than 5%, greater than 20%, greater than 50%, from about 5% to about 20% by weight, or even from about 7.5% to about 15% by weight. The aromatic content is measured by Nuclear Magnetic Resonance (NMR) spectroscopy.

The composition can include a tackifying agent with a melt point of less than 100° C., or even less than 95° C.

The adhesive composition can include at least about 20% by weight, at least about 25% by weight, from about 10% by weight to about 60% by weight, from about 15% by weight to about 50% by weight, or even from about 20% by weight to about 45% by weight tackifying agent.

Plasticizer

The adhesive composition can include a plasticizer. Alternatively, the adhesive can be free of a plasticizer (i.e. contain no plasticizer). Suitable plasticizers include, e.g., naphthenic oils, paraffinic oils (e.g., cycloparaffin oils), mineral oils, phthalate esters, adipate esters, olefin oligomers (e.g., oligomers of polypropylene, polybutene, and hydrogenated polyisoprene), polybutenes, polyisoprene, hydrogenated polyisoprene, polybutadiene, benzoate esters, animal oil, plant oils (e.g. castor oil, soybean oil (e.g. high oleic soy oil), derivatives of oils, glycerol esters of fatty acids, polyesters, polyethers, lactic acid derivatives and combinations thereof.

Useful commercially available plasticizers include GALSOL 550 and CALSOL 5550, naphthenic oils from Calumet Specialty Products Partners, LP (Indianapolis, Ind.), KAYDOL OIL mineral oil from Sonneborn (Tarrytown N.Y.) PARAPOL polybutene from Exxon Mobil Chemical Company (Houston, Tex.), OPPANOL polyisobutylene from BASF (Ludwigsjhafen, Germany), KRYSTOL 550 mineral oil from Petrochem Carless Limited (Surrey, England), PURETOL 35 and 15 both mineral oils from Petro Canada Lubricants Inc. (Mississauga, Ontario), PLENISH from Pioneer Dupont, and TPC 5230, polyisobutylene available from TPC Group (Houston, Tex.).

The plasticizer can be a naphthenic oil. Alternately, the plasticizer includes aromatic or naphthenic groups.

The plasticizer can be present in the adhesive composition in an amount of at least about 5% by weight, at least about 10% by weight, at least about 15% by weight, at least about 18% by weight, no greater than about 10% by weight, no greater than about 15% by weight, from about 5% to about 30% by weight, or even from about 15% to about 25% by weight.

Wax

The adhesive composition can include a wax. Useful classes of wax include, e.g., paraffin waxes, microcrystalline waxes, high density low molecular weight polyethylene waxes, by-product polyethylene waxes, polypropylene waxes, Fischer-Tropsch waxes, oxidized Fischer-Tropsch waxes, functionalized waxes such as acid, anhydride, and hydroxy modified waxes, animal waxes, vegetable waxes (e.g. soy wax) and combinations thereof. Useful waxes are solid at room temperature and preferably have a Ring and Ball softening point of from 50° C. to 170° C. Useful waxes are commercially available from a variety of suppliers including EPOLENE N and C series of trade designations from Westlake Chemical Corporation (Houston, Tex.) including e.g. EPOLENE N-21 and the LICOCENE series of trade designations from Clariant International Ltd. (Muttenz, Switzerland) including e.g. TP LICOCENE PP 6102.

The adhesive composition can include no greater than about 8.0% by weight, no greater than about 5% by weight, from about 1% by weight to about 7.5% by weight, or even from about 1% to about 5% by weight wax.

Additional Polymers

The adhesive composition optionally includes additional polymers e.g. single-site catalyzed polyooefins, amorphous poly-alpha olefins, polyethylene homopolymers/copolymers and polypropylene homopolymers/copolymers.) Useful additional polymers include VISTAMAXX 6102 (propylenelethylene copolymer available from ExxonMobil Chemical (Houston, Tex.) and REXTAC 2730 (an amorphous poly-alpha olefin) available from Rextac LLC (Odessa, Tex.).

The adhesive composition includes a total polymer content (including SBC and additional polymers) of at least about 35% by weight, at least about 40% by weight, from about 35% by weight to about 60% by weight, or even about 50% by weight to about 70% by weight.

Additional Components

The adhesive composition optionally includes additional components including, e.g., stabilizers, antioxidants, adhesion promoters, ultraviolet light stabilizers, corrosion inhibitors, odor absorbers/neutralizers, colorants (e.g., pigments and dyes), fragrances, fillers (e.g. nano particles, clay, talc), surfactants, wetness indicators, superabsorbents, coextrusion coatings, processing aids and combinations thereof.

Useful antioxidants include, e.g., pentaerythritol tetrakis [3,(3,5-di-tert-butyl-4-hydroxyphenyl)propionate], 2,2'-methylene bis(4-methyl-6-tert-butylphenol), phosphites including, e.g., tris(p-nonylphenyl)-phosphite (TNPP) and bis(2,4-di-tert-butylphenyl)4,4'-diphenylene-diphosphonite, di-stearyl-3,3'-thiodipropionate (DSTDP), and combinations thereof. Useful antioxidants are commercially available under a variety of trade designations including, e.g., the IRGANOX series of trade designations including, e.g., IRGANOX 1010, IRGANOX 565, and IRGANOX 1076 hindered phenolic antioxidants and IRGAFOS 168 phosphite antioxidant, all of which are available from BASF Corporation (Florham Park, N.J.), and ETHYL 702 4,4'-methylene bis(2,6-di-tert-butylphenyl). When present, the adhesive composition preferably includes from about 0.1% by weight to about 2% by weight antioxidant.

Disposable Article

The adhesive compositions and elastic composites of this invention can be incorporated into any suitable article including personal care garments, medical garments and industrial worker garments.

The elastic composite of this invention is useful in a variety of applications and constructions to improve comfort and fit including e.g., disposable absorbent articles including, e.g., diapers, training paints, swim wear, absorbent underpants, adult incontinence products, sanitary napkins, medical dressings (e.g., wound care products and bandages), surgical pads, medical gowns, caps, gloves, drapes, face masks, laboratory coats, coveralls, meat-packing products, and components of absorbent articles including, e.g., an absorbent element, absorbent cores, impermeable layers (e.g., backsheets), tissue (e.g., wrapping tissue), acquisition layers and woven and nonwoven web layers (e.g., top sheets, absorbent tissue).

The elastic composite of this invention is useful for elasticizing many areas of disposable articles including leg cuffs, waist portions, belly bands, side panels and fastening tabs/ears. The elastic composite of this invention can further be use to elasticize any portion of the disposable article or even the entire disposable article.

EXAMPLES

Test Procedures

Test procedures used in the examples and throughout the specification, unless stated otherwise, include the following.

Viscosity Test Method

Viscosity is determined in accordance with ASTM D-3236 entitled, "Standard Test Method for Apparent viscosity of Adhesives and Coating Materials," (Oct. 31, 1988), using a Brookfield Thermosel viscometer Model RVDV 2 and a number 27 spindle. The results are reported in centipose (cps).

Melt Flow Rate

Melt Flow Rate was run according to ASTM D 1238 at the conditions stated.

Test Lamination Preparation

Test laminations were prepared by continuous slot coating the elastic adhesive composition between two nonwoven* substrates at an application temperature of 177° F., a nip pressure of 15 pounds per square inch (PSI), and a run speed of at least 20 ft/min. Laminations were prepared with an adhesive coatweight of 100 gms (Controls 1-2, Ex. 3-5) and 130 gsm (Ex. 1-2) and the width of the adhesive was at least 3 inches. A sufficient amount of laminate is prepared such that at least 60 inches of representative lamination can be collected for testing.

*For Controls 1-2 and Examples 1-3, the nonwoven used is carded, hydroentangled and comprises 50/50 (PET/PP). It has a basis weight of 28 g/m² and a cross direction tensile strength of 15 Newtons/5 cm.
*For Examples 4 and 5, the nonwoven used is carded, hydroentangled and comprises 50/50 (PET/PP). It has a basis weight of 25 g/m² and a cross direction tensile strength of 12 Newtons/5 cm.

Peel Force Test Method

Test laminates were prepared by coating adhesive between two substrates according to the Test Lamination Preparation method above. Peel force is determined using ASTM D1876-01 entitled; "Test Method for Determining Peel Resistance of Adhesive (T-Peel Test Method)," with the exception that the test is run at a rate of 12 inches per minute, instead of 10 in per minute, over a period of 10 seconds, and 7 replicates are run instead of the 10 specified in ASTM D1876. The samples are run on an INSTRON type-test instrument. The test samples are 1 inch in width and at least 4 inches in length. The average peel force over 10 seconds of peeling is recorded, and the results are reported in grams. The initial peel force is measured at least 24 hours after the laminate is prepared.

2-Peak Hysteresis Test Method

Test laminates were prepared by coating adhesive between two substrates according to the Test Lamination Preparation method above. Test samples are prepared by cutting the laminates in cross-web direction, with 1 inch in width and at least 3 inches in length. The test is conducted at least 24 hours after the non woven laminate is prepared.

The strips prepared are extended to a certain strain (e.g. 50%, 100%, 150% or 200%) and then retracted to their original dimension. Subsequently the specimen goes through a second extension-retraction cycle with the same deformation. The cross head speed is set to 20 inches per minute. There is no holding time between extension and retraction. The samples are run on an INSTRON type-test instrument with at least 3 replicates. The permanent set after each cycle, peak load/stress at maximum deformation, and percent energy loss between each cycles are recorded.

1-Peak Hysteresis Test Method

Testing is performed using an INSTRON type-test instrument with a cross head speed of 20 inches per minute, for both extension and retraction. The test specimen is two inches in width. Grip separation is also set to two inches. A sample test set normally consists of five replicates. The elastic is elongated by the grips until a force of 10 Newtons is reached. At that point the specimen is placed in a hold for 30 seconds and then allowed to retract to the point where the specimen returns to the two inch initial gap setting. The data collected is the percent elongation (mm/mm and/or percent) at which the specimen 10 Newtons. During the 30 second hold, the force will diminish over this time, and the magnitude of the loss in force is reported as force relaxation in Newtons (N). After the 30 second hold time has passed, the specimen is returned to the two inch gap. The percent (%) set of the specimen is measured by the distortion of the two inch specimen length, determined by the % elongation of the specimen immediately after the cross head returns to the original gap as the three on the elastic approaches zero.

Polymer Descriptions

Polymer Example 1 is a <1 weight % diblock, SIS tri-block co-polymer containing 30% by weight styrene and having a MFR of 168 g/10-min (190° C., 2.16 kgs).

Kraton MD 1648 is a <10 weight % diblock, selectively hydrogenated SBS co-polymer containing 20% by weight styrene and having a MFR of 30 g/10-min (190° C., 2.16 kgs).

Vector 4411A is a <1 weight % diblock, SIS tri-block co-polymer containing 44% by weight styrene and having a MFR of 9 g/10-min (190° C., 2.16 kgs).

Vector 6241A is a <1 weight % diblock, SBS tri-block co-polymer containing 43% by weight styrene and having a MRF of 5.0 g/10-min (190° C., 2.16 kgs).

TABLE ONE

|  | Control 1 | Control 2 | Ex. 1 | Ex. 2 | Ex. 3 | Ex. 4 | Ex. 5 |
|---|---|---|---|---|---|---|---|
| VECTOR 4411 | 46.5 |  |  | 23 |  |  |  |
| VECTOR 6241 |  | 46.5 | 20 |  |  |  |  |
| KRATON MD 1648 |  |  |  |  |  | 45 | 59.5 |
| Polymer Example 1 |  |  | 26 | 23 | 59.5 |  |  |
| Avg. Styrene Content of SBC (weight %) | 44 | 43 | 35.7 | 37 | 30 | 20 | 20 |
| ESCOREZ 5690 | 29.75 | 29.75 | 31.5 | 29.75 |  |  |  |
| ESCOREZ 5615 |  |  |  |  |  |  |  |
| ESCOREZ 5400 |  |  |  |  | 40 |  |  |
| ESCOREZ 5415 |  |  |  |  |  | 29.5 | 30 |
| CALSOL 550 | 23.25 | 23.25 | 22 | 23.25 |  |  |  |
| PURETOL 35 |  |  |  |  |  | 25 | 10 |
| IRGANOX 1010 | 0.5 | 0.5 | 0.5 | 0.5 | 0.5 | 0.5 | 0.5 |

TABLE TWO

|  | Control 1 | Control 2 | Ex. 1 | Ex. 2 | Ex. 3 | Ex. 4 | Ex. 5 |
|---|---|---|---|---|---|---|---|
| Viscosity (cps) |  |  |  |  |  |  |  |
| @149° C. (300° F.) | 35,150 | 37,800 | 17,800 | 11,500 | 43,000 | 5,400 | 34,500 |
| @163° C. (325° F.) | 14,250 | 18,850 | 8,850 | 5,750 | 23,200 | 3,290 | 17,300 |
| @177° C. (350° F.) | 7,050 | 12,050 | 5,925 | 3,480 | 13,350 | 2,300 | 10,200 |
| Viscosity Ratio @149° C./@177° C. | 4.99 | 3.11 | 3.00 | 3.30 | 3.22 | 2.35 | 3.38 |
| 2-Peak Hysteresis Testing |  |  |  |  |  |  |  |
| 50% hysteresis |  |  |  |  |  |  |  |
| Set 1st cycle (%) | 6 | 5 | 9 | 7 | 9 | 5 | 2 |
| Set 2nd cycle (%) | 7 | 6 | 11 | 9 | 10 | 8 | 4 |
| Energy loss (%) | 35.1 | 34.5 | 41.6 | 35 | 34.9 | 57.1 | 50 |
| 100% hysteresis |  |  |  |  |  |  |  |
| Set 1st cycle (%) | 16 | 14 | 26 | 20 | 23 | 15 | 9 |
| Set 2nd cycle (%) | 18 | 16 | 30 | 23 | 26 | 25 | 12 |
| Energy loss (%) | 46.9 | 45.6 | 57.3 | 51.0 | 51.1 | 67.9 | 61 |
| 150% hysteresis |  |  |  |  |  |  |  |
| Set 1st cycle(%) | 26 | 23 | 49 | 36 | 41 | 30 | 15 |
| Set 2nd cycle (%) | 28 | 27 | 54 | 40 | 45 | 50 | 21 |
| Energy loss (%) | 56.2 | 54.4 | 67.2 | 62.4 | 61.9 | 76 | 70.2 |
| 1-Peak Hysteresis Testing |  |  |  |  |  |  |  |
| Extension at 10N (%) | 122.9 |  |  |  | 40.7 | 120 | 127 |
| Force Relaxation (N) | 4.5 |  |  |  | 3.9 | 6.4 | 5.0 |
| Set (%) | 25.1 |  |  |  | 10.9 | 26 | 11 |

TABLE TWO-continued

|  | Control 1 | Control 2 | Ex. 1 | Ex. 2 | Ex. 3 | Ex. 4 | Ex. 5 |
|---|---|---|---|---|---|---|---|
| Adhesion | | | | | | | |
| Average peel (gram force) | 68 | 272 | Substrate failure | Substrate failure | Substrate failure | Substrate failure* | Substrate failure* |

*Bonds were pulled by hand

What is claimed is:

1. An elastic composite comprising:
   a first and second substrate; and
   a hot melt adhesive composition between the first and second substrates thereby permanently bonding the first and second substrates to each other and providing elasticity in the bonded area, said hot melt adhesive comprising:
   at least 15% of s styrene block copolymer with a melt flow rate of at least 15 g/10 minutes (190° C., 2.16 kgs) and a diblock content of no greater than 10% by weight, and
   from 5% by weight to 30% by weight plasticizer,
   wherein the hot melt adhesive composition has a viscosity of no greater than about 20,000 cps at 350° F.,
   wherein the first and second substrate are selected from the group consisting of a nonwoven and a polymer film,
   and further wherein the hot melt adhesive has a set $1^{st}$ cycle after 50% hysteresis when tested according to the 2-Peak Hysteresis Test Method of no more than 12%.

2. The elastic composite of claim 1 wherein the hot melt adhesive composition has a set $1^{st}$ cycle after 50% hysteresis of no more than 10%.

3. The elastic composite of claim 1 wherein the hot melt adhesive composition has a viscosity of no greater than 5,000 cps at 350° F.

4. The elastic composite of claim 1 wherein the hot melt adhesive composition further comprises a tackifying agent.

5. The elastic composite of claim 1 wherein the styrene block copolymer has an unsaturated mid-block.

6. The elastic composite of claim 1 wherein the first and second substrate are nonwoven.

7. The elastic composite of claim 6 wherein the nonwoven comprising the first and second substrates is airlaid, carded and hydroentangled.

8. The elastic composite of claim 6 wherein the first and second substrate are nonwovens extensible to greater than 100% in the cross web direction.

9. A disposable article comprising the elastic composite of claim 1.

10. The disposable article of claim 9 wherein the elastic composite is used in an application selected from the group consisting of ear, waist band, and belly band and side panel.

11. The disposable article of claim 9 selected from the group consisting of diaper, adult incontinence product, feminine hygiene product and medical bandage.

12. A hot melt adhesive composition that can be used to create a bonded, elasticized region, comprising:
   from 50% to 70% by weight one or more styrene block copolymers, wherein the one or more styrene block copolymers comprises at least 20% by weight of a styrene-isoprene-styrene block copolymer with a melt flow rate of at least 15 g/10 minutes (190° C., 2.16 kgs), and a diblock content of no greater than 10% by weight, a tackifying agent and,
   from 5% by weight to 30% by weight plasticizer,
   wherein the adhesive composition has a viscosity of no greater than 20,000 cps at 350° F.

13. The hot melt adhesive composition of claim 12 with a viscosity of no greater than 15,000 cps at 350° F.

14. The hot melt adhesive of claim 12 wherein the average styrene content of the styrene block copolymer is at least 30% by weight.

15. The hot melt adhesive composition of claim 12 wherein the one styrene block copolymer has a MFR (190° C./2.2 kg) of at least 50 g/10 minutes.

16. An elastic composite comprising:
   a substrate, and
   the hot melt adhesive composition of claim 12 bonded to the substrate;
   wherein the hot melt adhesive provides elasticity to the bonded area.

17. The hot melt adhesive of claim 12 wherein the hot melt adhesive composition is free of end block resin that has a melting point greater than 110° C.

18. The elastic composite of claim 1 wherein the styrene block copolymer is styrene-isoprene-styrene.

19. The elastic composite of claim 1 wherein the first and second substrate stretch with the hot melt adhesive composition.

20. The elastic composite of claim 6 wherein the nonwoven comprising the first and second substrates is selected from the group consisting of nonwoven extensible to greater than 100% in the cross-web direction and post treated nonwoven.

* * * * *